(12) United States Patent
Casagrande

(10) Patent No.: US 6,525,078 B1
(45) Date of Patent: Feb. 25, 2003

(54) COMPOUND FOR THE TREATMENT OF ATHEROSCLEROTIC-THROMBOTIC PATHOLOGICAL CONDITIONS

(76) Inventor: Cesare Casagrande, Via Campogallo, 21/67, 20020 Arese (Milano) (IT)

( * ) Notice: Subject to any disclaimer, the term of this patent is extended or adjusted under 35 U.S.C. 154(b) by 0 days.

(21) Appl. No.: 10/178,564

(22) Filed: Jun. 25, 2002

(51) Int. Cl.$^7$ ........................ C07D 213/02; A61K 31/44
(52) U.S. Cl. ........................ 514/357; 546/336
(58) Field of Search ........................ 546/336; 514/357

(56) References Cited

U.S. PATENT DOCUMENTS

| | | | |
|---|---|---|---|
| 3,725,417 A | 4/1973 | Holland | 546/265 |
| 3,973,026 A | 8/1976 | Orzalesi et al. | 424/263 |
| 4,294,833 A | 10/1981 | Innocenti et al. | 546/265 |
| 4,698,354 A | 10/1987 | De Regis et al. | 514/357 |

FOREIGN PATENT DOCUMENTS

EP      0 219 468      4/1987

OTHER PUBLICATIONS

Russell Ross, "Atherosclerosis—An Inflammatory Disease", The New England Journal of Medicine, vol. 340, No. 2, Jan. 14, 1999, pp. 115–126.
Bjarne Østerud, "A Global View on the Role of Monocytes and Platelets in Atherogenesis", Thrombosis Research, vol. 85, No. 1, 1997 pp. 1–22.
Artur–Aron Weber, et al., "Complex Control of Vascular Smooth Muscle Cell Growth by Thromboxane A$_2$", THROMB HAEMOST, vol. 80, 1998, pp. 207–208.
Tilo Grosser, et al., "Thromboxane A$_2$ induces cell signaling but requires platelet–derived growth factor to act as a mitogen", European Journal of Pharmacology, vol. 319, 1997, pp. 327–332.
Rajbabu Pakala, et al., "Effect of Serotonin, Thromboxane A$_2$, and Specific Receptor Antagonists of Vascular Smooth Muscle Cell Proliferation", Circulation, vol. 96, No. 7, Oct. 1997, pp. 2280–2286.
Agapios Sachindis, et al., "Thromboxane A$_2$ and Vascular Smooth Muscle Cell Proliferation", Hypertension, vol. 26, No. 5, Nov. 1995, pp. 771–780.
David A. Jones, et al., "Activation of Thromboxane and Prostacyclin Receptors Elicits Opposing Effects on Vascular Smooth Muscle Cell Growth and Mitogen–Activated Protein Kinase Signaling Cascades", Molecular Pharmacology, vol. 48, 1995, pp. 890–896.
Paul M. Vanhoutte, et al., "Vascular Endothelium: Vasoactive Mediators", Progress in Cardiovascular Disease, vol. 39, No. 3, 1996, pp. 229–238.

Ulrich Foerstermann, et al., "Response of Human Coronary Arteries to Aggregating Platelets: Importance of Endothelium–Derived Relaxing Factor and Prostanoids", Circulation Research, vol. 63, No. 2, 1988, pp. 306–312.
M. W. Radomski, et al., "The Anti–aggregating Properties of Vascular Endothelium: Interactions Between Prostacyclin and Nitric Oxide", Br. J. Pharmac, vol. 92, 1987, pp. 639–646.
Jacques Maclouf, et al., "Eicosanoids and Iso–Eicosanoids: Constitutive, Inducible and Transcellular Biosynthesis in Vascular Disease", THROMB HAEMOST, vol. 79, 1998, pp. 691–705.
Julio A. Rimarachin, et al., "Regulation of Cyclooxygenase–2 Expression in Aortic Smooth Muscle Cells", Arteriosclerosis and Thrombosis, vol. 14, vol. 7, Jul. 1994, pp. 1021–1031.
David Bishop–Bailey, et al., "Differential Induction of Cyclooxygenase–2 in Human Arterial and Venous Smooth Muscle", Arterioscler Thrombosis, vol. 18, 1998, pp. 1655–1661.
Jacek Nowak, et al., "Redirection of Prostagladin Endoperoxide Metabolism at the Platelet–Vascular Interface in Man", J. Clin. Invest., The American Society for Clinical Investigation, Inc., vol. 83, 1989, pp. 380–385.
Jos Vermylen, et al., "Thromboxane Synthase Inhibitors and Receptor Antagonists", Cardiovascular Drugs and Therapy, vol. 6, 1992, pp. 29–33.
Paolo Gresele, et al., "Thromboxane Synthase Inhibitors, Thromboxane Receptor Antagonists and Dual Blockers in Thrombotic Disorders", Trends Pharmacol Sci, vol. 12, 1991, pp. 158–163.
Michael Emerson, et al., "Endogenous Nitric Oxide Acts as a Natural Antithrombotic Agent in Vivo by Inhibiting Platelet Aggregation in the Pulmonary Vasculature", THROMB HAEMOST, vol. 81, 1999, pp. 961–966.
E. Bassenge, "Endothelium–mediated Regulation of Coronary Tone", Basic Research in Cardiology, vol. 86 (Suppl 2), 1990, pp. 69–76.
Daniela Salvemini, et al., "Nitric Oxide–mediated Cyclooxygenase Activation", J. Clin. Invest., The American Society for Clinical Investigation, Inc., vol. 97, No. 11, Jun. 1996, pp. 2562–2568.

*Primary Examiner*—Zinna Nothington Davis
(74) *Attorney, Agent, or Firm*—Oblon, Spivak, McClelland, Maier & Neustadt, P.C.

(57) ABSTRACT

4-Methoxy-N$^1$-(4-trans-nitrooxycyclohexyl)-N$^3$-(3-pyridinylmethyl)-1,3-benzenedicarboxamide and acid addition salts thereof with pharmaceutically acceptable organic and inorganic acids, and a pharmaceutical composition containing the same, for the treatment of vascular diseases involving atherosclerotic-thrombotic conditions and of other pathological conditions as shown in the description.

9 Claims, 1 Drawing Sheet

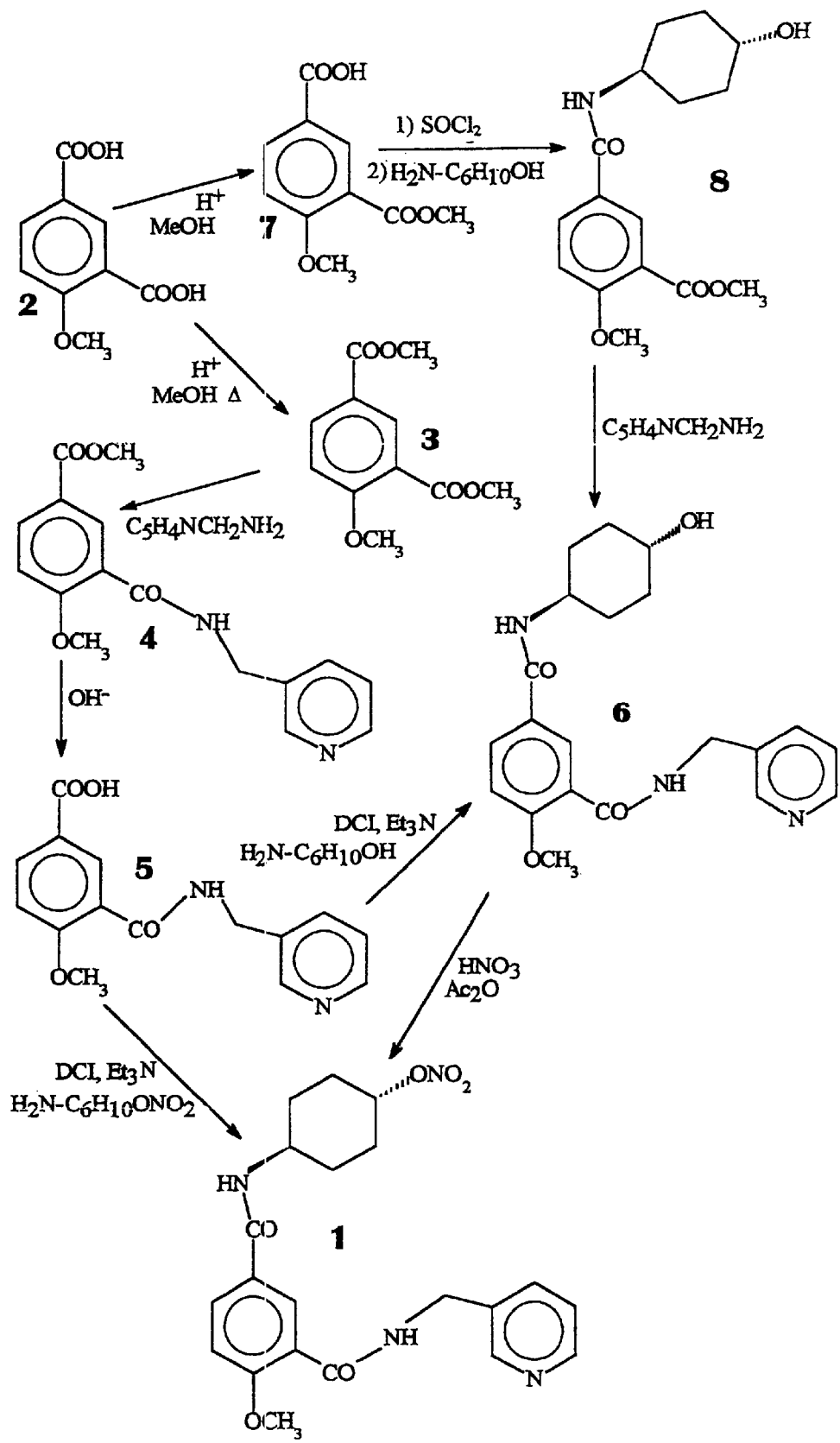

COMPOUND FOR THE TREATMENT OF ATHEROSCLEROTIC-THROMBOTIC PATHOLOGICAL CONDITIONS

FIELD OF THE INVENTION

This application is based on European Patent Application No. 01830413.9 filed on Jun. 21, 2001, the content of which is incorporated hereinto by reference.

The present invention relates to 4-methoxy-$N^1$-(4-trans-nitrooxycyclohexyl)-$N^3$-(3-pyridinylmethyl)-1,3-benzenedicarboxamide (formula 1 in FIG. 1) as a pharmacologically active compound in the treatment of vascular diseases.

More particularly, this invention relates to 4-methoxy-$N^1$-(4-trans-nitrooxycyclohexyl)-$N^3$-(3-pyridinylmethyl)-1,3-benzenedicarboxamide as well as the acid addition salts thereof with pharmaceutically acceptable organic or inorganic acids as pharmacologically active compounds in the treatment of atherosclerotic-thrombotic pathological conditions and other pathological conditions which can benefit from the inhibition of thromboxane $A_2$ and from a pharmacological supply of nitric oxide (NO).

The invention also relates to processes for the preparation of 4-methoxy-$N^1$-(4-trans-nitrooxycyclohexyl)-$N^3$-(3-pyridinylmethyl)-1,3-benzenedicarboxamide and the acid addition salts thereof with pharmaceutically acceptable organic or inorganic acids.

Furthermore, the invention relates to a pharmaceutical composition comprising 4-methoxy-$N^1$-(4-trans-nitrooxycyclohexyl)-$N^3$-(3-pyridinylmethyl)-1,3-benzenedicarboxamide or an acid addition salt thereof with pharmaceutically acceptable organic or inorganic acids, as an active ingredient, together with at least a pharmaceutically acceptable ingredient.

The invention also relates to a method of use of both said compound and said pharmaceutical composition in the treatment of said conditions.

BACKGROUND OF THE INVENTION

Evidence is growing for a dynamic interplay between the processes of thrombosis and atherosclerosis in the vascular system, starting from the initial development of vascular diseases and continuing in the dramatic events that are the cause of death and disability in a large section of the population. Diabetes, hypertension, tobacco smoke and unhealthy dietary habits are among the leading causes of these diseases.

Blood and vascular wall exert mutual influences in their physiological functions, which are mediated by the contact of blood cells (including platelets, which differ from other cells by lacking the cellular nucleus) with the vascular endothelial and smooth muscular cells, via mechanisms of adhesion and infiltration, and by the exchange of a number of biochemical mediators.

Most of these interactions are also involved in pathological processes, such as the development of acute vasospastic conditions, the formation of occlusive thrombi and the development of atherosclerotic plaques.

The role played by activated platelets has special relevance, since the present advancement of knowledge indicates that the pro-thrombotic and pro-atherogenic role of platelet activation is not limited to the initiation of the formation of thrombi starting from platelet aggregates, but it involves adhesion and the mutual interchange of biochemical mediators with the vascular wall, especially when the latter is pathologically altered, as in the case of endothelial lesions and of atherosclerotic plaques (R Ross, NE J Med 340 (1999) 115–126; B Osterud, Thromb Res 85 (1997) 1–22).

Platelet-released mediators have a role in vasospasms, a critical mechanism of various ischemic conditions, and in the proliferation of vascular smooth muscle, an essential step of the atherosclerotic process (AA Weber, K Schror, Thromb Haemost 80 (1998) 207–208; T Grosser et al, Eur J Pharmacol 319 (1997) 327–332; R Pakala et al, Circulation 96 (1997) 2280–2286; A Sachinidis et al, Hypertension 26 (1995) 771–780), which in turn, by the alteration of the vascular surface and the rupture of plaques contributes to platelet activation and has an immediate causative role in acute thrombotic and ischemic events.

Among the mediators released by platelets, thromboxane $A_2$, serotonin, and growth factors, such as PDGF and TGF-$\beta$1 are the most pathologically relevant.

On the other hand, the endothelial lining of the vascular wall, when not pathologically altered, opposes the actions of activated platelets by the release of mediators (DA Jones et at, Mol Pharmacol 48 (1995) 890–896; PM Vanhoutte, JV Mombouli, Progress in Cardiovascular Diseases 39 (1996) 229–238) such as EDRF (the endothelial derived relaxing factor, identified as NO, nitric oxide), and as prostacyclin. Both induce relaxation and reduce proliferation of the arterial wall, and counteract platelet aggregation and adhesion (U Forstermann et al, Circulation Res 63 (1988) 306–312; MW Radomski et al, Br J Pharmacol 92 (1987) 639–646).

Cellular interactions of platelets, blood cells, and vascular cells have special relevance in the synthesis of a cascade of metabolites of arachidonic acid, the eicosanoids (J Macloufet al, Thromb Haemost. 79 (1998) 691–705). Arachidonic acid is converted by the enzymatic action of the cyclooxygenases, into the endoperoxides $PGG_2$ and $PGH_2$. These metabolites are further converted into thromboxane $A_2$ and into prostacyclin $PGI_2$, as wells as into $PGE_2$, $PGD_2$ and other prostaglandins, by the enzymatic action of specific synthetases.

Owing to the different cellular locations of these enzymes, the transcellular exchange of the precursor arachidonic acid (which is also carried by fragmented platelets) and, most importantly, of the endoperoxides $PGG_2$ and $PGH_2$ exerts significant influence in the generation of the biologically active eicosanoids, and among them thromboxane $A_2$ and prostacyclin. Important amount of endoperoxides are formed in platelet and in endothelial cells under the influence of cyclooxygenase-1. These amount predominate in normal conditions, over those produced in other cells, such as lymphocytes (including the monocyte-macrophage type) and vascular smooth muscle cells.

The synthesis of endoperoxides can however be amplified, in pathological situations, by the induction, in all the above cells, but not in platelets, of the formation of large amounts of cyclooxygenase-2. The induction is mediated by pro-inflammatory stimuli, and is marked in atherosclerosis-damaged tissues (JA Rimarachin et al, Arterioscler Thromb 14 (1994) 1021–1031; D Bishop-Bailey et al, ibid, 18 (1998) 1655–1661). It has to be noted that eicosanoids generation, via cyclooxygenase-1 and/or cyclooxygenase-2 has important physiological and pathological roles, in addition to those elicited within the circulatory system, in various body organs.

According to their respective physiological role, platelets are abundantly endowed with thromboxane synthetase, as endothelial cells are with prostacyclin synthetase.

Thromboxane $A_2$, acting as an inducer of irreversible platelet aggregation and also representing an amplifying signal of platelet activation, has a key role in platelet-vascular wall interactions not only because of its direct action, but also for the stimulation of the release of the other vasospastic and proliferative mediators generated by platelets and for the progression of the fissuring of atherosclerotic plaques, leading to occlusive vascular events.

The efforts of developing clinical applications of drugs acting by inhibition of thromboxane $A_2$ have been enacted by different approaches. The first therapeutic approach directed to the inhibition of the synthesis of thromboxane $A_2$ has been based on the use of acetylsalicylic acid, which is now known to be able to inhibit cyclooxygenase-1 selectively and irreversibly; the therapeutic usefulness has been clinically demonstrated, but the blockade of the first, common step of the synthesis of the eicosanoids brings together the inhibition the synthesis of physiologically beneficial prostaglandins in the circulatory system, in particular prostacyclin, and also of prostaglandins performing a protective role in gastric and renal tissues by maintaining perfusion and cytoprotection.

The benefit of this pharmacological approach is thus limited by undesirable effects. Furthermore, acetylsalicylic acid proved to be unable to inhibit the inducible cyclooxygenase-2, therefore leaving an open way to the productions of thromboxane $A_2$ in inflamed tissues of the circulatory and respiratory system and in other body organs.

A second pharmacological approach has been targeted to the suppression of the synthesis of thromboxane $A_2$ by specific inhibition of thromboxane synthetase, without hindering the synthesis of the other eicosanoids, and in particular prostacyclin (J Nowak, GA FitzGerald, J Clin Invest 83 (1989) 380–385).

Furthermore, a third approach has been also explored, not aimed at inhibiting the synthesis of thromboxane, but at hindering its effect on platelets and on vascular tissue by using agents able to exert an antagonistic action at thromboxane receptors (TP receptors).

These latter two approaches (J Vermylen, H Deckmyn, Cardiovascular Drugs and Therapy, 6 (1992) 29–33) have led to a number of clinical studies, but have not yet offered a valid alternative to the use of acetylsalicylic acid.

It has been reasoned that competitive antagonists are probably not adequate to fully antagonize the large amount of thromboxane $A_2$ produced by aggregating platelets, while on the other hand, during thromboxane synthetase inhibition at the endoperoxide stage, the increased concentrations of intermediate endoperoxides exerted on tromboxane receptors effects similar to those of thromboxane itself. Therefore, the possible benefits of the combination of these two pharmacological approaches in single pharmacological agents exerting a dual action, such as picotamide (4-methoxy-$N^1$, $N^3$-bis-(3-pyridinylmethyl)-1,3-benzenedicarboxide) or ridogrel (5-[3-pyridinyl-3-(trifluoromethyl) phenylmethyleneaminooxy]pentanoic acid), have also been suggested (P Gresele et al, Trends Pharmacol Sci 12 (1991) 158–163).

In conclusion, the proposed pharmacological agents addressed to the direct inhibition of thromboxane have not yet reached general acceptance in medical practice, and only acetylsalicylic acid has an established and consolidated use as an antithrombotic agent, notwithstanding its limitations and unwanted effects.

Organic nitrates, such as nitroglycerin or isosorbide mono and dinitrate, have a well established clinical use, which is however confined to the exploitation of their vasodilator properties. In recent years, a better understanding of the pharmacological action of various precursors of NO on platelets and on the vascular wall has been achieved, following the identification of EDRF (endothelium derived relaxing factor) as nitric oxide, NO, and the clarification of its physiological role. This advancement of knowledge has been applied both to organic nitrates, and to new NO-donors, carrying nitrate or nitrite functions, or other chemical function easily converted to NO, and also to the biochemical precursor of endogenous NO, L-arginine. The advancement has led to the suggestion that, in addition to their known vasodilator action, the NO-donors may interact with pharmacological agents acting on the cascade of the metabolites of arachidonic acid, either in counteracting stimuli of platelet activation, vasoconstriction, and vascular cell proliferation (M Emerson et al, Thromb Haemost 81 (1999) 961–966; E Bassenge, Basic Res Cardiol 86 (suppl 2, 1990) 69–76), or by a direct modulation of the synthesis of eicosanoids (D Salvemini et al, J Clin Invest 97 (1996) 2562–2568).

Therefore a strong medical need still exists of increasedly effective antithromboxane agents for the prevention and the therapy of vascular atherosclerotic-thrombotic diseases and of other pathological conditions. The inventors perceived that more favourable therapeutic effects can be achieved by decreasing the synthesis of thromboxane $A_2$, while at the same time inhibiting its actions, and also pharmacologically supplying nitric oxide.

OBJECTS OF THE INVENTION

It is therefore an object of this invention to provide a compound useful in the treatment of vascular diseases.

It is another object of this invention to provide a compound useful in the treatment of atherosclerotic-thrombotic pathological conditions.

It is yet another object of this invention to provide a compound having both antithromboxane and NO-donor action.

It is a further object of this invention to provide processes for the preparation of the compound having the above mentioned properties.

It is still another object of this invention to provide a pharmaceutical composition comprising the compound having the above mentioned properties as an active ingredient together with at least a pharmaceutically acceptable ingredient.

It is a further object of this invention to provide a method of treatment comprising administering to a human being suffering from a vascular pathological condition, such as atherosclerotic-thrombotic diseases, and of other conditions which can benefit from inhibition of thromboxane $A_2$ and from a pharmacological supply of nitric oxide, an effective amount of a compound having the above mentioned properties.

These and other objects of the invention are achieved by 4-methoxy-$N^{1-(}$4-trans-nitrooxycyclohexyl)-$N^3$-(3-pyridinylmethyl)-1,3-benzenedicarboxamide and the acid addition salts thereof with pharmaceutically acceptable organic or inorganic acids.

BRIEF DESCRIPTION OF THE FIGURES

FIG. 1 shows some synthetic pathways for the preparation of 4-methoxy-$N^1$-(4-trans-nitrooxycyclohexyl)-$N^3$-(3-pyridinylmethyl)-1,3-benzenedicarboxamide of formula 1.

BRIEF DESCRIPTION OF THE INVENTION

The inventors have found that 4-methoxy-$N^1$-(4-trans-nitrooxycyclohexyl)-$N^3$-(3-pyridinylmethyl)-1,3-benzenedicarboxamide of formula 1 and the acid addition salts thereof with pharmaceutically acceptable organic or inorganic acids are endowed with both antithromboxane and NO-donor action.

Furthermore, it has been found that the compound of the invention is effective and advantageous in the treatment of atherosclerotic-thrombotic conditions affecting the vascular system and in the treatment of other pathological conditions which can benefit from the inhibition of thromboxane $A_2$ and from a pharmacological supply of nitric oxide, or NO.

More particularly the compound of the invention is endowed with a novel pharmacological profile particularly suitable to the treatment of the said pathological conditions, being able to exert a combination of pharmacological actions related to a) the inhibition of the synthesis of thromboxane $A_2$, b) the inhibition of the effects exerted by thromboxane $A_2$ and by some other metabolites of arachidonic acid through the activation of specific receptors (TP receptors), and c) the release of nitric oxide.

DETAILED DESCRIPTION OF THE INVENTION

Accordingly, this invention provides 4-methoxy-$N^1$-(4-trans-nitrooxycyclohexyl)-$N^3$-(3-pyridinylmethyl)-1,3-benzenedicarboxamide and acid addition salts thereof with pharmaceutically acceptable organic and inorganic acids.

The invention also provides a process for preparing 4-methoxy-$N^1$-(4-trans-nitrooxycyclohexyl)-$N^3$-(3-pyridinylmethyl)-1,3-benzenedicarboxamide comprising:

a) reacting the dimethyl ester of 4-methoxy-1,3-benzene dicarboxylic acid with 3-pyridinylmethylamine to yield regioselectively the corresponding 3-monoamide-1-ester;

b) hydrolyzing in an alkaline medium said 3-monoamide-1-ester to the corresponding 3-monoamide-1-carboxylic acid;

c) reacting said 3-monoamide-1-carboxylic acid with an coupling agent and a cyclohexylamine derivative and, when required, converting the thus obtained compound into 4-methoxy-$N^1$-(4-trans-nitrooxycyclohexyl)-$N^3$-(3-pyridinylmethyl)-1,3-benzenedicarboxamide.

Typically, in step c) the coupling agent is carbonyldiimidazole.

Furthermore, in step c) the cyclohexylamine derivative is trans-4-nitrooxycyclohexylamine, thus yielding 4-methoxy-$N^1$-(4-trans-nitrooxycyclohexyl)-$N^3$-(3-pyridinylmethyl)-1, 3-benzenedicarboxamide.

Alternatively, in step c) the cyclohexylamine derivative is trans-4-hydroxy cyclohexylamine, thus yielding the $N^1$-4-trans-hydroxycyclohexyl-$N^3$-(3-pyridinylmethyl)-1,3-benzenedicarboximide, which is then reacted with nitric acid to yield 4-methoxy-$N^1$-(4-trans-nitrooxycyclohexyl)-$N^3$-(3-pyridinylmethyl)-1,3-benzenedicarboxamide.

The present invention further provides another process for preparing 4-methoxy-$N^1$-(4-trans-nitrooxycyclohexyl)-$N^3$-(3-pyridinylmethyl)-1,3-benzenedicarboxamide comprising:

a) reacting 4-methoxy-1,3-benzenedicarboxylic acid with methanol in the presence of sulphuric in mild conditions to yield regioselectively the corresponding 3-monomethyl ester 1-carboxylic acid;

b) converting said 3-monomethyl ester 1-carboxylic acid into the corresponding acyl chloride and reacting with trans-4-hydroxycyclohexylamine to yield the corresponding 1-amide-3-ester;

c) reacting the thus obtained 1-amide-3-ester with 3-pyridinylmethylamine to yield $N^1$-4-trans-hydroxycyclohexyl-$N^3$-(3-pyridinylmethyl)-1,3-benzenedicarboxamide;

d) reacting $N^1$-4-trans-hydroxycyclohexyl-$N^3$-(3-pyridinylmethyl)-1,3-benzenedicarboxamide with nitric acid to yield 4-methoxy-$N^1$-(4-trans-nitrooxycyclohexyl)-$N^3$-(3-pyridinylmethyl)-1,3-benzenedicarboxamide.

Furthermore, this invention provides a pharmaceutical composition comprising 4-methoxy-$N^1$-(4-trans-nitrooxycyclohexyl)-$N^3$-(3-pyridinylmethyl)-1,3-benzenedicarboxamide or an acid addition salt thereof with a pharmaceutically acceptable organic or inorganic acid together with at least a pharmaceutically acceptable ingredient.

The present invention also provides a method of treatment comprising administering to a human being suffering from a pathological condition which can benefit from the inhibition of thromboxane $A_2$ and from a supply of nitric oxide, or NO, an effective amount of 4-methoxy-$N^1$-(4-trans-nitrooxycyclohexyl)-$N^3$-(3-pyridinylmethyl)-1,3-benzenedicarboxamide or an acid addition salt thereof with a pharmaceutically acceptable organic or inorganic acid.

Tipically, said pathological conditions include vascular atherosclerotic-thrombotic diseases, diabetic vasculopathies, diabetic nephropathy, diabetic retinopathy, male vasculogenic erectile disfunctions, pulmonary hypertension, asthma, chronic obstructive pulmonary disease, ulcerative colitis, Crohn's disease, colonic polyposis.

Indeed, the compound of this invention is endowed with a novel pharmacological profile particularly suitable to the treatment of atherosclerotic-thrombotic pathological conditions, being able to exert a combination of pharmacological actions related to a) the inhibition of the synthesis of thromboxane $A_2$, b) the inhibition of the effects exerted by thromboxane $A_2$ and by some other metabolites of arachidonic acid through the activation of specific receptors (TP receptors), and c) the release of nitric oxide, or NO.

Accordingly, the compound of this invention exerts favourable effects on the cardiovascular system and in other organ by exploiting the synergic actions of a) decreasing the synthesis of thromboxane $A_2$ in cells endowed with either cyclooxygenase-1 or –2 without hindering the synthesis of prostacyclin and the other prostaglandins, and on the contrary making the intermediate endoperoxides available for the synthesis of these eicosanoids, b) inhibiting the actions of any residual thromboxane $A_2$, as well as those of the endoperoxides, exerted through the stimulation of the TP receptors, and c) releasing nitric oxide and thus implementing the action of prostacyclin and other prostaglandins on platelets, on the circulatory system and on other organs.

These properties can find useful therapeutic application in vascular diseases which involve atherosclerotic-thrombotic pathological conditions, and also can find application in other pathological conditions which can be improved by the inhibition of thromboxane $A_2$ and by pharmacologically supplying nitric oxide, such as diabetic vasculopathies, diabetic nephropathy, diabetic retinopathy, male vasculogenic erectile disfunctions, pulmonary hypertension, asthma, chronic obstructive pulmonary disease, ulcerative colitis, Crohn's disease, colonic polyposis.

Platelet Aggregation

Platelet aggregation experiments were performed on platelet-rich plasma (PRP) prepared from blood of healthy human subjects, who had not taken cyclooxygenase inhibitors (acetylsalicylic acid, non-steroidal anti-inflammatory agents) for at least two weeks. Blood was collected in test tubes containing a 3.2% sodium citrate solution (1/10 of blood volume) and immediately centrifuged at 150×g for 15 minutes. Samples of PRP were further centrifuged at 12,000×g in order to obtain platelet-poor plasma (PPP), used for calibration of light transmittance of the double-channel aggregometer, fixing the transmittance of PRP as 10% and that of PPP as 90%. Platelet aggregation in PRP of each subject was tested measuring the percent increase in transmittance under the addition of increasing amounts of sodium arachidonate, in concentrations in the range from 300 to 900 $\mu$M, or of collagen, in concentrations in the range from 0.5 to 2.5 $\mu$g/ml, or of U-46619, in concentrations in the range from 0.2 to 1.6 $\mu$M. (U-46619, i.e., 9,11-dideoxy-11$_\alpha$, 9$_\alpha$-epoxymethano-prostaglandin $F_{2\alpha}$ is an active synthetic analogue of thromboxane $A_2$ and it is chemically stable, at difference from the natural compound; it is therefore used as a substitute in pharmacological experiments). In this way the threshold concentration, i.e., the concentration inducing a submaximal irreversible aggregation was assessed in each subject with the three agents.

PRP samples of subjects not responding to the maximal concentrations were discarded. The threshold concentrations were applied to induce aggregation on samples of PRP of each subject, after the addition, followed by 10 min incubation, of the compounds to be tested in a series of concentrations in the range from $10^{-7}$ M to $10^{-3}$ M. The individual values of percent inhibition from 4–6 subjects were used in the calculation of the $IC_{50}$.

4-Methoxy-$N^1$-(4-trans-nitrooxycyclohexyl)-$N^3$-(3-pyridinylmethyl)-1,3-benzenedicarboxamide showed $IC_{50}$ respectively of $12\times10^{-6}$ M for arachidonic acid, $22\times10^{-6}$ M for collagen, and $33\times10^{-6}$ M for U-46619. The ability to counteract platelet aggregation by arachidonic acid in these experimental conditions was shared by various agents, including an inhibitor of cyclooxygenase, such as acetylsalycilic acid, an inhibitor of thromboxane synthetase, such as ozagrel, i.e., (E)-3-[4-(1H-imidazol-1-ylmethyl)-phenyl]-2-propenoic acid (Merck Index, 11th ed, 6935) and an antagonist of the TP receptor, such as daltroban, i.e., p-[2-(p-chlorobenzenesulfonamido)ethyl]phenylacetic (Merck Index, 11th ed, 2807). On the contrary, the ability to counteract the aggregation by U-46619 was shared only by daltroban, and not by acetylsalicylic acid or ozagrel. Furthermore, ozagrel up to $10^{-3}$ M concentrations did not show any significant inhibitory activity in the aggregation induced by collagen.

Thromboxane Synthesis

Test compounds were added in a series of concentrations ranging from $10^{-7}$ M to $10^{-3}$ M to samples of blood from healthy human subjects, who had not taken cyclooxygenase inhibitors (acetylsalicylic acid, non-steroidal anti-inflammatory agents) for at least two weeks. The blood samples were allowed to clot for 60 min in a bath at 37° C., and then centrifuged at 2500×g for 10 min. The serum was separated and kept frozen at −20° C. for the determination of $TxB_2$ by radio immunoassay. $TxB_2$ is the stable metabolite into which thromboxane $A_2$ is rapidly converted. Compound 4-methoxy-$N^1$-(4-transnitrooxycyclohexyl)-$N^3$-(3-pyridinylmethyl)-1,3-benzenedicarboxamide was shown to inhibit thromboxane synthesis with an $IC_{50}$ of $18\times10^{-6}$ M. In this assay an antagonist of thromboxane receptors, such as daltroban, did not show any effect, at difference from acetylsalicylic acid and ozagrel.

Prostacyclin Synthesis

The effects on the transcellular synthesis of prostacyclin from endoperoxides generated in platelets were assessed by layering platelet rich plasma (PRP), obtained from healthy human subjects as described above, on cultured bovine endothelial cells ($5\times10^5$ cells/well). The endothelial cells were pretreated with acetylsalicylic acid ($10^{-4}$ M) in order to inhibit the direct synthesis of endoperoxides, and washed twice with Dulbecco's phosphate buffered saline. Then to individual samples of endothelial cells there were added at 37° C. while shaking on an oscillating platform, 0.5 ml of PRP samples pretreated with the test compounds in various concentrations, ranging from $10^7$ M to $10^{-3}$ M. Collagen (0.5 $\mu$g/ml) was then added to each sample. After 2 minutes of contact at 37° C., PRP was removed and centrifuged at 12,000×g, and the supernatant was frozen and kept at −20° C. for the determination of 6-keto-prostaglandin $F_{1\alpha}$ by radioimmunoassay.

6-Keto-prostaglandin $F_{1\alpha}$ is a stable metabolite into which prostacyclin is rapidly converted. 4-Methoxy-$N^1$-(4-trans-nitrooxycyclohexyl)-$N^3$-(3-pyridinylmethyl)-1,3-benzenedicarboxamide, starting from $10^{-6}$ M concentration, markedly increased the production of the prostacyclin metabolite, which was completely inhibited in acetylsalicylic acid-treated cells, up to 800–1600 $\mu$pg/ml, a level 8–16 times higher of the amount produced in basal conditions by endothelial cells not submitted to cyclooxygenase inhibition with acetylsalicylic acid. Daltroban, a competitive antagonist of thromboxane receptor, did not stimulate the synthesis of prostacyclin in this test.

Vascular Relaxation

The ability to induce vascular relaxation by acting as a donor of nitric oxide was tested in vitro on rabbit aortae. Rings of aortae were suspended in a Krebs-Henseleit solution at 37° C., submitted to a 1 g tension and connected to a force transducer. Tissue contraction was induced with norepinephrine ($10^{-6}$ M) and the test compounds were added in increasing concentrations in the range from $10^{-8}$ M to $10^{-3}$ M. Compound 4-methoxy-$N^1$-(4-trans-nitrooxycyclohexyl)-$N^3$-(3-pyridinylmethyl)-1,3-benzenedicarboxamide induced a complete relaxation of the aortic ring at a concentration of $10^{-4}$ M, with a calculated $EC_{50}$ of $3.2\times10^{-6}$ M.

When methylene blue, an inhibitor of soluble guanylate cyclase able to counteract the effects of nitric oxide, was added to the bath in $10^{-5}$ M concentration, the compound was still able to relax the aortic tissue, but the concentration-response curve appeared to be shifted toward higher concentrations, with a calculated $EC_{50}$ of $55\times10^{-6}$ M. The compound was shown to be similarly able to produce relaxation in aortic rings contracted with 5-hydroxytryptamine or with U-46619.

Therapeutic Applications

Owing to its pharmacological properties the compound of this invention finds its main therapeutic application in pathological conditions involving thrombotic and atherosclerotic alterations in various stages of development, as a primary or a secondary treatment. As a primary treatment it can be administered to patients assessed for pathological symptoms and/or signs of cardiovascular risks, such as hypertension, diabetes, hyperlipidemias, along with unhealthy habits, such as alimentary, alcoholic, or tobacco smoke excesses, in order to prevent the progression of the disease and the frequently occurring cardiovascular and cerebrovascular accidents and disfunctions, which include vasospastic and thrombotic arterial obstructions, unstable angina, myocardial infarction, transient cerebral ischemia, stroke, diabetic vasculopathies, peripheral vascular occlusions, pulmonary thrombotic embolism, pulmonary hypertension, diabetic nephropathy, renal failure, diabetic retinopathy. As a secondary treatment it can be administered to patients having suffered from the above mentioned accidents and disfunctions, in order to resolve the sequelae and to prevent their reoccurrence. It can also be administered during and following medical and surgical procedures aimed at restoring blood perfusion of affected organs, such as thrombolysis, balloon angioplasty and stenting, and coronary artery by-pass, in order to increase the probability of success of the procedures and to avoid late restenosis and reocclusion.

The therapeutic use of the compound of this invention appears to be even more advantageous and preferable in those patients in which the use acetylsalicylic acid has to be avoided because of the occurrence, or risk, of adverse effects such as gastric damage, reduction of renal perfusion, or asthmatic attacks. It is also advantageous in those patients in which the atherosclerotic-thrombotic disease is concomitant with elevated blood pressure or with respiratory dysfunctions of the respiratory system, such as pulmonary hypertension, chronic obstructive pulmonary disease, and asthma In these patients the suppression of thromboxane action, while preserving prostacyclin synthesis, and the vasodilation and bronchodilation induced by NO can beneficially combine with the pharmacological action of other specific treatments. In particular, it can be mentioned that the adverse effect of cough, frequently induced by antihypertensive ACE inhibitors can be suppressed, thus rendering the antihypertensive treatment sustainable and effective.

Furthermore the compound of this invention can be administered to patients suffering from other diseases which can benefit from the inhibition of thromboxane and a supply of nitric oxide, such as patients suffering from respiratory ailments, such as asthma and chronic obstructive pulmonary disease, or patients suffering from colonic diseases such as ulcerative colitis, Crohn's disease, colonic polyposis.

Pharmaceutical Compositions

For practical purposes 4-methoxy-$N^1$-(4-trans-nitrooxycyclohexyl)-$N^3$-(3-pyridinylmethyl)-1,3-benzenedicarboxamide and the acid addition salts thereof with pharmaceutically acceptable organic or inorganic acids may be administered as they are, but it will be preferred to administer them as pharmaceutical compositions.

These compositions will contain a therapeutic amount 4-methoxy-$N^1$-(4-transnitrooxycyclohexyl)-$N^3$-(3-pyridinylmethyl)-1,3-benzenedicarboxamide or an equivalent amount of an acid addition salts thereof with a pharmaceutically acceptable organic or inorganic acids, together with liquid or solid pharmaceutical carriers. If required for a particular therapy, the compositions of this invention may also contain other compatible active ingredients, whose contemporaneous administration is therapeutically useful.

The dosage forms of the pharmaceutical compositions of this invention may be solid, such as tablets, sugar-coated pills, capsules, powders, or semi-liquid, such as creams and ointments, or liquid, such as solutions, suspensions and emulsions. Further dosage forms are patches for transdermal delivery, suppositories and microenemas for rectal and colonic delivery, and inhalers for bronchial delivery of powders, or suspensions or solutions.

These dosage forms can be compounded for oral, peroral, sublingual, transdermal, parenteral, rectal or bronchial administration, and furthermore they can be compounded for the prompt release, or for the sustained release, of the active ingredient.

In addition to conventional carriers, the compositions of this invention may contain other suitable pharmaceutical additives, such as preservatives, stabilizers, emulsifiers, salts to regulate osmotic pressure, organic or inorganic compound as solubilizers or buffers, colouring and flavouring agents.

The preferred mode of administration, being conveniently applicable in simple dose schedules both in short and long term therapeutic treatments in most patients, is the oral route, including the peroral or sublingual route. Preferred formulations are tablets or capsule for oral administration, granulated powders for extemporaneous suspension for oral administration, or tablets for sublingual administration. It is also possible, however, to resort to other routes of administration, as required by the conditions of the patients to be treated, such as the transdermal route, the parenteral route, the bronchial route, or the rectal route, suitably preparing transdermal ointments, creams, gels, or patches, sterile solution or suspension for parenteral use, powders or suspensions or solution for bronchial inhalation, and suppositories or microenemas for rectal administration.

For therapeutic purposes the effective amount of 4-methoxy-$N^1$-(4-trans-nitrooxycyclohexyl)-$N^3$-(3-pyridinylmethyl)-1,3-benzenedicarboxamide can vary depending on various factors such as the particular therapy required, the pharmaceutical composition, and the method of administration.

Preferably, a dosage form of this invention, suitable for single or multiple daily administration, will contain from 10 to 600 mg of 4-methoxy-$N^1$-(4-trans-nitrooxycyclohexyl)-$N^3$-(3-pyridinylmethyl)-1,3-benzenedica or the equivalent amount of an acid addition salt thereof.

Advantageously, the total daily dosage will be of from 10 to 1800 mg and, even preferably of from 50 to 600 mg.

Nevertheless, the optimal effective amount for single administration and/or for the total daily dosage can be adjusted by simple routine procedures, according to the need of the therapy and of the individual patient.

The pharmaceutical compositions of this invention can be prepared according to conventional techniques known to the person skilled in the art, which comprise admixing, granulating and compressing, when necessary, or variously mixing or dissolving the active ingredients, together with suitable carriers, when appropriate to obtain the desired result.

Synthesis

FIG. 1 shows some preparation pathways of 4-methoxy-$N^1$-(4-trans-nitrooxy cyclohexyl)-$N^3$-(3-pyridinylmethyl)-1,3-benzenedicarboxamide of formula 1 starting from 4-methoxy-1,3-benzenedicarboxylic acid (formula 2) and providing for the regioselective introduction of two different amidic substituents on the 1- and 3-carboxyl groups.

It has been found that the dimethyl ester of this acid, having formula 3, which can be easily obtained from the acid, preferably and in high yield by boiling in methanol in the presence of sulphuric acid, can be regioselectively converted the 3-N-sustituted amide 1-monoester of formula 4 by reaction with 3-pyridinylmethylamine. The reaction is preferably carried out by heating at from 50 and 80° C. in the presence of an excess of the amine, which can be easily recovered.

Furthermore, it has been found that acid-amide having formula 5, which can be obtained from compound 4 with conventional methods by alkaline hydrolysis of the ester function, can be transformed into the $N^1,N^3$-disubstituted amide of formula 6 by activation of the carboxylic function followed by reaction with trans-4-hydroxycyclohexyl amine; the activation is achieved by adding a coupling agent, preferably carbonyldiimidazole, or alternatively a carbodiimide, such as dicyclohexylcarbodiimide, or a clorocarbonate ester, such as methyl chloroformiate. By employing carbonyldiimidazole, the reaction can be carried out at room temperature in a non-reactive solvent, and the desired diamide can be easily purified with good yields. The diamide 6 can thereafter be transformed into the compound of formula 1 by esterification with nitric acid in mild conditions, a preferred method being the interaction with a reactive mixture of nitric acid and acetic anhydride at 0° C.

As an alternative, trans-4-hydroxycyclohexylamine can be preliminarily converted into the corresponding nitric ester, and then the coupling reaction of the latter with acid 5, previously activated using carbonyldiimidazole as a preferred coupling agent, leads directly to the desired compound 1.

A second regioselective synthetic approach to the key intermediate diamide of formula 6 can also be used, since it has been found that the 3-monomethyl ester of 4-methoxy-1,3-benzenedicarboxylic acid, having formula 7, can be directly and selectively obtained by esterification of the acid with sulphuric acid in methanol at room temperature in a yield of over 50%, and furthermore the by-products of the reaction, which are the dimethyl ester of formula 3 and unreacted 4-methoxy-1,3-benzenedicarboxylic acid, are easily separated from the product and almost quantitatively recovered for further use. Previously 4-methoxy-1,3-benzenedicarboxylic acid 3-monomethyl ester had been obtained mixed with the corresponding 1-monomethylester or by complex methods, e.g., via 4-amino-1,3-benzenedicarboxylic acid 3-monomethyl ester (U.S. Pat. No. 3,725,417). The monoester of formula 7 can be converted into the chloride by conventional methods and then into the amide-ester of formula 8 by reaction with trans-4-hydroxycyclohexylamine. From the amide-ester of formula 8, the diamide of formula 6 can again be obtained by taking advantage of the reactivity of the 3-carboxylic ester function with 3-pyridinylmethylamine, in similar conditions to those already defined for the formation of compound 4.

The production of 4-methoxy-$N^1$-(4-trans-nitrooxycyclohexyl)-$N^3$-(3-pyridinylmethyl)-1,3-benzenedicarboxamide according the synthetic approaches of this invention outlined in FIG. 1 may also be enacted by changing one or more of the reagent and one of more of the reaction conditions described above and in the following examples, by using chemical techniques which are well known to the expert of the art. Furthermore, 4-methoxy-$N^1$-(4-trans-nitrooxycyclohexyl)-$N^3$-(3-pyridinylmethyl)-1,3-benzenedicarboxamide may be incorporated in pharmaceutical compositions as it is or following its combination in an acid addition salts with a pharmaceutically acceptable organic or inorganic acid.

The following examples are intended to further illustrate this invention without, however, limiting it in any way.

EXAMPLE 1

Methyl 4-Methoxy-3-(3-pyridinylmethylaminocarbonyl)benzoate (Formula 4)

To 50 g of 4-methoxy-1,3-benzenedicarboxylic acid (formula 2) dissolved in 400 ml of methanol there were added 18 ml of concentrated sulphuric acid, d 1.84, and the mixture was boiled at reflux for 7 hours. The mixture was poured into 600 ml of ice-water. The precipitated 4-methoxy-1,3-benzenedicarboxylic acid dimethyl ester (formula 3) was collected, washed by suspending in a solution of sodium hydrogen carbonate and then in water, and dried, yielding 52 g (91%) of compound 4 as a white solid, m.p. 96–97° C. It showed in $^1$-NMR in DMSO-$d_6$ δ 3.84 (s, 3H, COOMe); 3.95 (s, 3H, PhOMe); 3.96 (s, 3H, COOMe); 7.28 (d, 1H, $H_a$), 8.1 (dd, 1H, $H_b$); 8.2 (d, 1H, $H_c$).

It was then dissolved in 150 ml of 3-pyridinylmethylamine and heated at 70° C. for 40 hours. Thereafter most of the excess amine was recovered by distillation in a vacuum. The residue was mixed with ice-water, acidified (pH 5) with diluted hydrochloric acid and extracted with chloroform. The extracts were dried with anhydrous sodium sulphate and evaporated, and the residue was taken up with light petroleum, b.p. 70–80° C., yielding 43.8 g (63%) of methyl 4-methoxy-3-(3-pyridinylmethylaminocarbonyl)benzoate (formula 4) as a white solid, the $^1$H-NMR spectrum of which in $CDCl_3$ showed signals at δ 3.91 (s, 3H, COOMe), 4.03 (s, 3H, PhOMe), 4.72 (d, 2H, PyCH$_2$); 7.05 (d, 1H, Ha); 7.31 (m, 1H, $H_{b,Py}$); 7.74 (m, 1H, $H_{c,Py}$); 8.1 (broad t, 1H, CONH); 8.19 (dd, 1H, $H_b$); 8.55 (broad m, 1H, $H_{a,Py}$); 8.62 (broad m, 1H, $H_{d,Py}$); 8.9 (d, 1H, $H_c$).

EXAMPLE 2

4-Methoxy-$N^1$-4-trans-hydroxycyclohexyl-$N^3$-(3-pyridinylmethyl)-1,3-benzenedicarboxamide (Formula 6)

To a solution of 42 g of methyl 4-methoxy-3-(3-pyridinylmethylaminocarbonyl)benzoate (formula 4) in 150 ml of methanol there were added under stirring at 20° C. 100 ml of a 10% solution of sodium hydroxide. The mixture was stirred at 20° C. for 3 hours, then 50 ml of water were added. The solution was washed with ethyl acetate, and thereafter it was kept under reduced pressure in order to remove methanol by evaporation. The pH was adjusted to 6 by adding 6N hydrochloric acid, and the precipitate was collected, dried and triturated in chloroform, yielding 36 g (90%) of the corresponding acid, m.p. 192–193° C., showing in the $^1$H-NMR spectrum in DMSO-$d_6$ signals at δ 3.98 (s, 3H, PhOMe), 4.52 (d, 2H, PyCH$_2$); 7.23 (d, 1H, Ha); 7.38 (m, 1H, $H_{b,Py}$); 7.72 (m, 1H, $H_{c,Py}$); 8.04 (dd, 1H, $H_b$); 8.27(d, 1H, $H_c$); 8.46 (m, 1H, $H_{a,Py}$); 8.56 (m, 1H, $H_{d,Py}$); 8.87 (broad t, 1H, CONH); 12.86 (broad s, 1H, COOH) (previously described in U.S. Pat. No. 4,698,354 via a different method; physical properties were not reported).

The above acid was dissolved in 250 ml of pure, dried methylene chloride and treated with 24 g of carbonyldiimidazole. The mixture was stirred for one hour at room temperature, resulting in a solution to which 22 g of the hydrochloride of trans-4-hydroxycyclohexylamine and 20 ml of triethylamine were added. The mixture was stirred at room temperature for 20 hours, then 200 ml of a 2% solution of sodium hydroxyde was added with stirring. The desired diamide separated as a white precipitate, and was collected, washed with water and dried. A further amount was obtained by evaporation of the separated methylene chloride fase, and was also washed with water and dried. The two fractions were combined and recristallized from chloroform, yielding 36.2 g (75%) of 4-methoxy-$N^1$-4-trans-hydroxycyclohexyl-$N^3$-(3-pyridinylmethyl)-1,3-benzenedicarboxamide (formula 6), m.p. 183–184° C.

The $^1$H-NMR spectrum in DMSO-$d_6$ showed signals at δ 1.4 (m., 4H); 2.1 (m, 5H); 3.69 (m, 1H, CHOH); 4.0 (m, 4H, PhOMe and CHNH); 4.7 (d, 2H, PyCH$_2$); 6.1 (broad d, CONHcy); 7.1 (d, 1H, Ha); 7.3 (m, 1H, H$_{b,Py}$); 7.71 (m, 1H, H$_{c,Py}$); 8.15 (dd, 1H, H$_b$); 8.25 (broad t, 1H, CONHPy); 8.48(d, 1H, H$_c$); 8.55 and 8.65(each m, 1H, H$_{a,Py}$ and H$_{d,Py}$).

EXAMPLE 3

4-Methoxy-N$^1$-4-trans-hydroxycyclohexyl-N$^3$-(3-pyridinylmethyl)-1,3-benzenedicarboxamide
(Formula 6)

4-Methoxy-1,3-benzenedicarboxylic acid 3-monomethyl ester (formula 7) was prepared by adding at 20° C. under stirring 12 ml of concentrated sulphuric acid, d 1.84, to a suspension of 50 g of 4-methoxyisophthalic acid in 400 ml of methanol; stirring was then continued for 1 hour and then the mixture was poured into ice-water (400 ml). The precipitate was collected and stirred with a saturated solution of sodium hydrogen carbonate; the insoluble residue (15 g) was constituted by 4-methoxy-1,3-benzenedicarboxylic acid dimethyl ester. The filtered solution was adjusted to pH 4.8 by adding 6N hydrochloric acid, thus precipitating the desired monoester, which was collected and washed with water, yielding 28.1 g (52.5%) of white solid. By further acidification of the mother liquor unreacted 4-methoxy-1,3-benzenedicarboxylic acid (9 g) was precipitated and collected. In this way a total recovery of 44.2% was obtained by summing together the recovery of the acid and the dimethyl ester, thus allowing a useful yield of 96.7%.

The monomethylester showed in $^1$-NMR in DMSO-d$_6$ δ 3.8 (s, 3H, COOMe); 3.91 (s, 3H, PhOMe); 7.28 (d, 1H, H$_a$), 8.1 (dd, 1H, H$_b$), 8.23 (d, 1H, H$_c$), 12.9 (s, broad, 1H, COOH)

The monoester (21 g) and 100 ml of thionyl chloride were boiled at reflux for 3 hours. The excess thionyl chloride was evaporated and the residue was dissolved in 60 ml of tetrahydrofuran and gradually added to a stirred mixture of triethylamine (20 ml) and trans-4-hydroxycyclohexylamine hydrochloride (17 g) in 100 ml of tetrahydrofuran, while keeping the temperature at 15° C. The mixture was stirred overnight at room temperature, and then diluted with water and stirred for 2 hours at room temperature and extracted with methylene chloride. The organic phase was washed with water and evaporated under reduced pressure; the residue was taken up in 250 ml of 1N hydrochloric acid and triturated, and then washed with water, collected and dried, yielding 24.5 g of crude methyl 2-methoxy-5-[(trans-4-hydroxycyclohexyl) aminocarbonyl] benzoate (formula 8), which was directly dissolved in 100 ml of 3-pyridinylmethylamine by heating at 70° C. Heating with stirring was continued for 40 hours. Most of the excess amine was recovered by distillation in a vacuum. The residue was taken up in water, and the mixture was adjusted to pH 6 with 6N hydrochloric acid. The aqueous phase was discarded, the product was dissolved in 500 ml of 1N hydrochloric acid. The solution was filtered from some insoluble material, adjusted to pH 9 with a 10% solution of sodium hydroxide, and extracted with chloroform/methanol (9:1). The extracts were submitted to flash chromatography on silica gel. The appropriate fractions (checked by tic on silica gel F254 plates, CHCl$_3$:MeOH=85:15, UV light) were combined and evaporated. The residue was taken up in chloroform-light petroleum, yielding 17.3 g (45%) of 4-methoxy-N$^1$-4-trans-hydroxycyclohexyl-N$^3$-(3-pyridinylmethyl)-1,3-benzenedicarboxamide, m.p. 182–183° C.

EXAMPLE 4

4-Methoxy-N1-(4-trans-nitrooxycyclohexyl)-N$^3$-(3-pyridinylmethyl)-1,3-benzenedicarboxamide
(Formula 1)

Nitric acid (d 1.49, 25 ml) was added under stirring at 0° C. to 100 ml acetic anhydride. After a few minutes, 31.5 g of 4-methoxy-N$^1$-4-transhydroxycyclohexyl-N$^3$-(3-pyridinylmethyl)-1,3-benzenedicarboxamide were gradually added in portion at the same temperature. At the end the stirring was continued for 10 minutes, and then the solution was poured with caution in a mixture of ice-water and sodium hydrogen carbonate, keeping pH at a neutral value. The light-yellow precipitated was collected, and dissolved in ethyl acetate. The solution was washed with a 5% solution of sodium hydrogen carbonate, dried with anhydrous sodium sulphate and evaporated under reduce pressure. The residual solid was taken up in a small volume of ethyl acetate, cooled and collected, yielding 26.7 g (76%) of 4-methoxy-N$^1$-(4-trans-nitrooxycyclohexyl)-N$^3$-(3-pyridinylmethyl)-1,3-benzenedicarboxamide, m.p. 153–154° C. The $^1$H-NMR spectrum in DMSO-d$_6$ showed signals at δ 1.5 (m., 4H); 2.2 (m, 4H); 4.0 (s, 3H, PhOMe+m, 1H); 4.65 (d, 2H, PyCH$_2$); 4.9 (m, 1H, CHONO$_2$); 6.45 (broad d, CONHcy); 7.05 (d, 1H, Ha); 7.1 (m, 1H, H$_{Py}$); 7.7 (m, 1H, H$_{Py}$); 8.1 (dd, 1H, Hb); 8.3 (broad t, 1H, CONHPy); 8.5 (m, 2H) and 8.6 (m, 1H, H$_{Py}$)

EXAMPLE 5

4-Methoxy-N$^1$-(4-trans-nitrooxycyclohexyl)-N$^3$-(3-pyridinylmethyl)-1,3-benzenedicarboxamide
(Formula 1)

trans-4-Hydroxycyclohexylamine (21 g) was gradually added at −15° C. to 45 ml of nitric acid, d 1.51. The mixture was stirred at 0° C. for 1.5 hours, and then poured into 300 ml of cooled diethyl ether. The separated nitrate salt was washed with ether, and then added in portions to a cooled and stirred mixture of 15 g of potassium carbonate, 15 ml of water and 200 ml of methylene chloride. The saline phase was extracted with methylene chloride and the combined organic phase was dried with anhydrous sodium sulphate and evaporated under reduce pressure to a residual volume of 100 ml, consisting in a solution of trans-4-nitrooxycyclohexylamine 4-Methoxy-3-(3-pyridinylmethylaminocarbonyl)benzoic acid (36 g) was dissolved in 180 ml of pure, dried methylene choride and treated with 24 g of carbonyldiimidazole. The mixture was stirred for one hour at room temperature. To the resulting solution there were added 15 ml of triethylamine and the solution of trans-4-nitrooxycyclohexylamine. The mixture was stirred at room temperature for 20 hours, then 200 ml of a 5% solution of sodium hydrogen carbonate were added with stirring. The organic phase was separated and evaporated under reduced pressure; the residue was triturated in cold water, then dissolved again in methylene chloride, and dried on anhydrous sodium sulphate. The solvent was evaporated under reduce pressure and the product was taken up in a small amount of cold ethyl acetate, yielding 28.5 g (53%) of 4-methoxy-N$^1$-(4-trans-nitrooxycyclohexyl)-N$^3$-(3-pyridinylmethyl)-1,3-benzenedicarboxamide, m.p. 152–153° C.

EXAMPLE 6

Capsules for Oral Administration containing 4-methoxy-N$^1$-(4-trans-nitrooxycyclohexyl)-N$^3$-(3-pyridinylmethyl)-1,3-benzenedicarboxamide, 100 mg For a batch of 200,000 capsules, 4-methoxy-N$^1$-(4-transnitrooxycyclohexyl)-N$^3$-(3-pyridinylmethyl)-1,3-benzenedicarboxamide, 20 kg, is thoroughly mixed with microcrystalline cellulose, 5 kg.

Lactose, 9.6 kg, and microcrystalline cellulose, 5 kg are mixed, then polysorbate 80, 0.4 kg, is added while mixing. The two powder mixtures are combined, mixed together and sieved through a 20 mesh mechanical sieve, then filled into size 1 gelatin capsules

EXAMPLE 7

Sachets for Instantaneous Suspension containing 4-methoxy-$N^1$-(4-trans-nitrooxycyclohexyl)-$N^3$-(3-pyridinylmethyl)-1,3-benzenedicarboxamide, 150 mg For a batch of 100,000 sachets, polysorbate 80, 0.500 kg, is slowly added while mixing to lactose, 24.5 kg, which is then mixed with 4-methoxy-$N^1$-(4-trans-nitrooxycyclohexyl)-$N^3$-(3-pyridinylmethyl)-1,3-benzenedicarboxamide, 15 kg. The mixed powders are added to sucrose, 159 kg, and orange flavouring agent, 1 kg, and thoroughly mixed. Sachets are then filled with 2 g portions of the mixed ingredients and sealed. The sachet are suitable for the preparation of an instantaneous suspension in water for oral administration.

What is claimed is:

1. 4-Methoxy-$N^1$-(4-trans-nitrooxycyclohexyl)-$N^3$-(3-pyridinylmethyl)-1,3-benzenedicarboxamide and acid addition salts thereof with pharmaceutically acceptable organic and inorganic acids.

2. A process for preparing 4-methoxy-$N^1$-(4-trans-nitrooxycyclohexyl)-$N^3$-(3-pyridinylmethyl)-1,3-benzenedicarboxamide comprising:
   a. reacting the dimethyl ester of 4-methoxy-1,3-benzene dicarboxylic acid with 3-pyridinylmethylamine to yield regioselectively the corresponding 3-monoamide-1-ester;
   b. hydrolyzing in an alkaline medium said 3-monoamide-1-ester to the corresponding 3-monoamide-1-carboxylic acid;
   c. reacting said 3-monoamide-1-carboxylic acid with an coupling agent and a cyclohexylamine derivative and, when required, converting the thus obtained compound into 4-methoxy-$N^1$-(4-trans-nitrooxy cyclohexyl)-$N^3$-(3-pyridinylmethyl)-1,3-benzenedicarboxamide.

3. A process according to claim 2, wherein in step c) the coupling agent is carbonyldiimidazole.

4. A process according to claim 2, wherein in step c) the cyclohexylamine derivative is trans-4-nitrooxycyclohexylamine, thus yielding 4-methoxy-$N^1$-(4-trans-nitrooxycyclohexyl)-$N^3$-(3-pyridinylmethyl)-1,3-benzene dicarboxamide.

5. A process according to claim 2, wherein in step c) the cyclohexylamine derivative is trans-4-hydroxycyclohexylamine, thus yielding $N^1$-4-transhydroxycyclohexyl-$N^3$-(3-pyridinylmethyl)-1,3-benzenedicarboxamide.

6. A process according to claim 2, wherein $N^1$-4-transhydroxycyclohexyl-$N^3$-(3-pyridinylmethyl)-1,3-benzenedicarboxamide is reacted with nitric acid to yield 4-methoxy-$N^1$-(4-trans-nitrooxycyclohexyl)-$N^3$-(3-pyridinylmethyl)-1,3-benzenedicarboxamide.

7. A process for preparing 4-methoxy-$N^1$-(4-trans-nitrooxycyclohexyl)-$N^3$-(3-pyridinylmethyl)-1,3-benzenedicarboxamide comprising:
   a. reacting 4-methoxy-1,3-benzenedicarboxylic acid with methanol in the presence of sulphuric in mild conditions to yield regioselectively the corresponding 3-monomethyl ester 1-carboxylic acid;
   b. converting said 3-monomethyl ester 1-carboxylic acid into the corresponding acyl chloride and reacting with trans-4-hydroxycyclohexylamine to yield the corresponding 1-amide-3-ester;
   c. reacting the thus obtained 1-amide-3-ester with 3-pyridinylmethylamine to yield $N^1$-4-transhydroxycyclohexyl-$N^3$-(3-pyridinylmethyl)-1,3-benzenedicarboxamide;
   d. reacting $N^1$-4-trans-hydroxycyclohexyl-$N^3$-(3-pyridinylmethyl)-1,3-benzenedicarboxamide with nitric acid to yield 4-methoxy-$N^1$-(4-trans-nitrooxy cyclohexyl)-$N^1$-(3-pyridinylmethyl)-1,3-benzenedicarboxamide.

8. A pharmaceutical composition comprising 4-methoxy-$N^1$-(4-trans-nitrooxycyclohexyl)-$N^3$-(3-pyridinylmethyl)-1,3-benzenedicarboxamide or an acid addition salt thereof with a pharmaceutically acceptable organic or inorganic acid together with a pharmaceutically acceptable ingredient.

9. A method of treatment comprising inhibiting thromboxane $A_2$ and supplying nitric oxide in a human being suffering from a pathological condition selected from the group consisting of vascular atheroscleroticthrombotic diseases, diabetic vasculopathies, diabetic nephropathy, diabetic retinopathy, male vasculogenic erectile disfunctions, pulmonary hypertension, asthma, chronic obstructive pulmonary disease, ulcerative colitis, Crohn's disease, colonic polyposis, wherein it is administered an effective amount of 4-methoxy-$N^1$-(4-trans-nitrooxycyclohexyl)-$N^3$-(3-pyridinylmethyl)-1,3-benzenedicarboxamide or an acid addition salt thereof with a pharmaceutically acceptable organic or inorganic acid.

\* \* \* \* \*